United States Patent [19]

Nagy et al.

[11] 4,344,950

[45] Aug. 17, 1982

[54] PARENTERAL SOLVENT AND A PROCESS FOR THE PREPARATION OF STABLE SOLUTIONS CONTAINING SAME

[75] Inventors: Géza T. Nagy; Gábor Szepesi; Mária Gazdag, all of Budapest, Hungary

[73] Assignee: Richter Gedeon Vegyeszeti Gyar Rt., Budapest, Hungary

[21] Appl. No.: 201,509

[22] Filed: Oct. 28, 1980

[30] Foreign Application Priority Data

Feb. 11, 1979 [HU] Hungary .................................. RI 733

[51] Int. Cl.$^3$ .................. A61K 31/475; A61K 31/435
[52] U.S. Cl. ..................................... 424/262; 424/256; 424/358; 424/361
[58] Field of Search ................ 424/256, 262, 358, 361

[56] References Cited

U.S. PATENT DOCUMENTS

| | | | |
|---|---|---|---|
| 3,005,754 | 10/1961 | Granatek | 424/358 |
| 3,155,586 | 11/1964 | Reed et al. | 424/358 |
| 3,159,542 | 12/1964 | Remmers et al. | 424/358 |

*Primary Examiner*—Sam Rosen
*Attorney, Agent, or Firm*—Karl F. Ross

[57] ABSTRACT

A parenteral solvent suitable for injectable solutions of eburnamenines and dihydroeburnamenines is disclosed, said solvent containing a buffer having the ability to buffer the injectable solutions at given pH values, at least one stabilizing agent which includes parenterally acceptable aliphatic alcohols containing one or more hydroxy groups or water-miscible ethers thereof, 30 to 70% by weight water and optional preservatives, anaesthetics, and antioxidants.

8 Claims, No Drawings

PARENTERAL SOLVENT AND A PROCESS FOR THE PREPARATION OF STABLE SOLUTIONS CONTAINING SAME

FIELD OF THE INVENTION

The invention relates to solvents suitable for the preparation of injectable solutions containing eburnamenine and dihydroeburnamenine derivatives and a process for the preparation of stable aqueous solutions containing same.

BACKGROUND OF THE INVENTION

It has been disclosed that eburnamenine and dihydroeburnamenine derivatives of natural, semi-synthetic or synthetic origin possess anti-vascular spasmodic activity due to the peripheral resistance reducing effect thereof, and thus said compounds may be used for the treatment of vascular headaches originating from a functional vascular spasm or flow disturbances and hypertensive or arterioscterotic blood vessel crisis states. In spite of a higher dosage in case of oral administration the effect is slower than in the case of parenteral administration. If rapid activity is desirable, parenteral treatment is necessary in order to ensure a quick resorption.

Injectable solutions containing eburnamenine and dihydroeburnamenine derivatives are only partially known. The application thereof is particularly important from a therapeutic point of view, as these compounds also have brain vasodilator activity as opposed to the commercially available injectable solutions, possessing only hypotensive activity.

According to test results solutions of eburnamenine and dihydroeburnamenine derivatives with the conventionally used parenteral solvents are unstable and show a considerably lower activity in animal tests.

In FR-PS No. 2 191 891 a process is disclosed for the preparation of vincanol-containing solutions and lyophilized injectable compositions. The pH-value of the thus prepared aqueous solutions ranges from 6 to 7 and the solutions are rather unstable. According to our investigations the molecule is considerably isomerized at this pH-value. The preparation of the lyophilized molecule is at the same time less economical and according to the disclosure a solution containing not more than 2.5 mg. of vincanol per ml. may be prepared.

In the conventional aqueous solutions containing vincaminic acid methyl ester epimerization and in the aqueous solutions containing apovincaminic acid ethyl ester ester hydrolysis occur; thus the effectivity of such solutions becomes lower. A parenteral solvent is required, which is suitable for the preparation of stable injectable solutions from eburnamenine and dihydroeburnamenine derivatives of the formula I

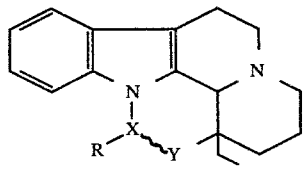

(I)

wherein
X ~ y is

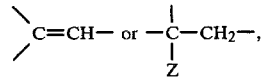

wherein Z is hydroxy or cyano and
R is hydrogen, an alkoxycarbonyl group having 2 to 6 carbon atoms which can be substituted by one or more halogen atoms or hydroxy groups or an aralkoxycarbonyl group.

DESCRIPTION OF THE INVENTION

We have now found that if the above active ingredients are dissolved in a solvent containing a suitable buffer and a stabilizer stable solutions are obtained.

The parenteral solvent according to the present invention comprises (a) a pharmaceutically acceptable buffer or an organic acid having $pK_a=3$ to 5 capable of adjusting the pH value of the solution to 2.5 to 5, preferably to 3.0 to 3.5 in the case of the compounds of the formula I, wherein
X ~ y is

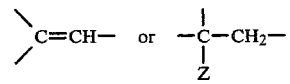

and Z is hydroxy or cyano, and
is hydrogen, an alkoxycarbonyl having 2 to 6 carbon atoms which can be substituted by one or more hydroxy groups or halogen atoms or an aralkyloxycarbonyl, provided that if
Z is hydroxy, than R may not stand simultaneously for hydrogen and
to a pH-value of 7.5 to 9.5, preferably to 8.0 to 8.5 in case of the compounds of the formula I wherein
X ~ Y is

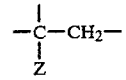

and Z is hydroxy and
R is hydrogen—

(b) one or more stabilizers in the form of aliphatic alcohols containing one or more hydroxy groups and/or water-miscible ethers thereof;

(c) 30–70% by weight water; and (d) optional preservatives, anaesthetics and/or antioxidants.

In order to adjust the pH of the solvent according to the invention such buffers and organic acids having a $pK_a$ of 3 to 5 may be employed which are physiologically indifferent and parenterally acceptable. As examples borax-boric acid, aminoacetic acid-sodium hydroxide, sodium acetate-acetic acid, citric acid-secondary sodium phosphate buffer, tartaric acid or citric acid can be used.

The aliphatic alcohol used as stabilizer is water soluble at the used concentration and is a parenterally acceptable aliphatic alcohol containing one or more hydroxy groups and/or an ether thereof such as alkanols having 2 to 6 carbon atoms, for example ethanol, glycols, such as propylene glycol, ethers of polyvalent alcohols, such as ethylene glycol monoethyl-ether, diethylene glycol monoethyl ether, polyethylene glycols and sugar alcohols, such as sorbitol and mannitol. Alkanols, for example ethanol, are preferably used in amount of about 5%, glycols, for example propylene glycol, in an amount of about 30%, glycolethers in an amount of about 50% and sugar alcohols in an amount of about 10% related to the total amount of the solvent.

The solvent according to the invention, which may be employed by the physician to dissolve the above active ingredients ex tempore, as well, may further contain known preservatives, for example organic mercury salts or benzyl alcohol and local anaesthetics and antioxidants.

The invention also provides for a process for the preparation of stable aqueous solutions containing as active ingredients a compound of the formula I and suitable for parenteral administration, characterized by dissolving the active ingredient in a medium which contains (a) a pharmaceutically acceptable buffer mixture or an organic acid having a $pK_a$-value of 3 to 5, capable of adjusting the pH of the solution to pH=2 to 5, preferably 3.0 to 3.5 in case of the compounds of the formula I

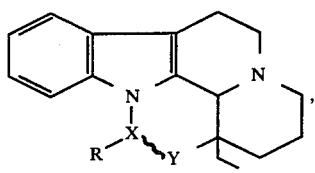
(I)

wherein
X ~ Y is

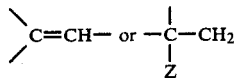

and Z is hydroxy or cyano, and

R represents hydrogen, an alkoxycarbonyl group having 2 to 6 carbon atoms which can be substituted by one or more halogen atoms and hydroxy groups or an aralkyloxycarbonyl group provided that if Z is hydroxy then R may not simultaneously stand for hydrogen, and to a pH-value of 7.5 to 9.5, preferably to 8.0 to 8.5, in the case of the compounds of the formula I, wherein
X ~ Y is

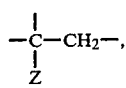

Z is hydroxy and
R is hydrogen, (b) one or more stabilizers in the form of aliphatic alcohols containing one or more hydroxy groups and/or water miscible ethers thereof;

(c) 30–70% by weight water; and (d) optionally preservatives, anaesthetics, and/or antioxidants.

SPECIFIC EXAMPLES

Further details of the invention are illustrated by the following Examples which serve merely as illustration and not for limitation.

EXAMPLE 1

In 35 ml. of sterile water for injection 54.4 mg. of boric acid and 68.8 mg. of sodium tetraborate $\times 10\ H_2O$ are dissolved at 25° C. Under stirring 80 mg. of lidocainehydrochloride, 4 ml. of ethanol and 40 ml. of ethylene glycol monoethyl ether and 0.8 mg. of phenyl mercury borate are added. The pH of the solution is 8.2 ± 1. The volume of the solution is completed to 80 ml. by adding water for injection. The solution is thoroughly homogenized, filtered and filled into sterile ampoules. Air is displaced from the ampoules with nitrogen gas, the ampoules are sealed and at 100° C. for 30 minutes sterilized by heat treatment.

The content of the ampoules is suitable for dissolving vincanol by the physician.

In 2 ml. of the above solvent 10 mg. of vincanol are dissolved and thus an injectable solution suitable for parenteral, for example intramuscular administration, is obtained.

Vincanol is soluble in the above solvent even at a concentration of 10 mg./ml. whereas it is substantially insoluble in distilled water at the same pH.

EXAMPLE 2

One may proceed as disclosed in Example 1 with the exception that as a buffer 56.8mg. of aminoacetic acid and 4 ml. of 0.1 N sodium hydroxide solution are substituted for boric acid and sodium tetraborate.

EXAMPLE 3

400 mg. of tartaric acid and 3600 mg. of sorbitol followed by 800 mg. of benzyl alcohol are dissolved at 25° C. in 52 ml. of sterile water for injection. The volume of the solution is then completed to 80 ml. by adding sterile water for injection, the solution is thoroughly homogenized, filtered and filled to sterile ampoules. Air is displaced from the ampoules with nitrogen gas and the ampoules are sealed and sterilized by heat treatment at 100° C. for 30 minutes. The content of the ampoules is suitable for dissolving apovincaminic acid ethyl ester by a physician.

In 2 ml. of the above solvent 10 mg. of apovincaminic acid ethyl ester are dissolved and thus an injectable solution suitable for parenteral, e.g. intramuscular administration is obtained.

Apovincaminic acid is well soluble in the above solvent even at a concentration of 10mg./ml., whereas it is substantially insoluble in distilled water at the same pH-value.

EXAMPLE 4

One may proceed as described in Example 3 but 40 mg. of ascorbic acid and 80 mg. of sodium pyrosulfite are also dissolved in the solution. The thus obtained solvent is particularly suitable for dissolving apovincaminic acid ethyl ester.

EXAMPLE 5

In 35 ml. of sterile water for injection 76.8 mg. of sodium hydroxide are dissolved and subsequently 96 mg. of conc. acetic acid, 32 ml. of propylene glycol and 800 mg. of benzyl alcohol are added. The pH of the solution is 3.8 ±0.1. The volume of the solution is then completed to 80 ml. by adding sterile water. The solution is further processed and disclosed in Example 3. The obtained solvent is particularly suitable for dissolving apovincaminic acid ethyl ester.

EXAMPLE 6

In 35 ml. of sterile water for injection 4.8 mg. of sodium purosulfite and 1440 mg. of citric acid are dissolved and 1200 mg. of benzyl alcohol and 24 ml. of propylene glycol are added. The volume of the solution is then completed with sterile water for injection to 80 ml. and the solution is thoroughly homogenized, filtered and filled into sterile ampoules. Air is displaced from the ampoules by nitrogen gas and the ampoules are sealed and sterilized at 100° C. by a heat treatment for 30 minutes.

The content of the ampoules is suitable for dissolving vincaminic acid methyl ester by the physician.

In 1 ml. of the above 5 mg. of vincaminic acid methyl ester are dissolved and thus an injectable solution suitable for parenteral, for example, intramuscular administration is obtained.

Vincaminic acid methyl ester is soluble in the above solvent even at a concentration of 15 mg./ml. whereas the same compound is substantially insoluble in distilled water at the same pH-value.

EXAMPLE 7

In 35 ml. of sterile water for injection 1233 mg. of citric acid and 757 mg. of disodium hydrogen phosphatedihydrate are dissolved whereafter 32 ml. of polyethylene glycol 300 and 1200 mg. of benzyl alcohol are added. The pH-value of the solution is 3.3 ±0.1. The volume of the solution is then completed to 80 ml. by adding sterile water for injection and the solution is further processed as disclosed in Example 6. The obtained solvent is particularly suitable for dissolving vincaminic acid methyl ester.

EXAMPLE 8

In 35 ml. of injectable sterile water 49 mg. of sodium hydroxide are dissolved and subsequently 96 mg. of conc. acetic acid 24 ml. of polyethylene glycol, 300 and 1200 mg. of benzyl alcohol are added. The volume of the solution is then completed to 80 ml. by adding sterile water for injection and the solution is then further processed according to Example 6. The obtained solvent is particularly suitable for dissolving vincaminic acid methyl ester.

The stability of the injectable solutions prepared by using the solvents according to the invention are illustrated by the following tests, in the course of which the isovincanol content of the vincanol solution and the apovincamine and vincaminic acid ethyl ester content of the apovincaminic acid ethyl ester solution is determined.

The decomposition of the injectable solutions was tested by high pressure liquid chromatography. Vincanol solution was investigated on Varian 8500 type apparatus, detection wave length was 280 nm, as eluent a 95:5 mixture of chloroform and abs. ethanol was employed, flow rate: 20 ml./hour.

TEST METHOD 2.0 ml. of injectable solution is pipetted in a 50.0 ml. shaking funnel and 20ml. of 1% aqueous sodium carbonate solution are added. The solution is shaken out with 10 ml. of chloroform whereafter the chloroform layer is passed through anhydrous sodium sulphate into a 25ml. measuring flask. The aqueous layer is shaken out again with 5ml. of chloroform and passed to the measuring flask. 1.25 ml. of abs. ethanol is then pipetted to the measuring flask and the content of the flask is filled up to the sign with chloroform. 5 μl of the solution are chromatographed.

During the experiments such vincanol was used, which contained 3.96% isovincanol according to the chromatography as disclosed aboves. The following table includes the data measured ten days after the solution had been prepared.

| pH-value of the injection | Isovincanol-content % |
|---|---|
| 1.7 | 25.7 |
| 4.9 | 25.4 |
| 5.9 | 20.7 |
| 6.9 | 12.9 |
| 7.3 | 10.2 |
| 8.4 | 3.5 |
| 9.1 | 3.5 |

The transformation of vincanol to isovincanol—as a function of the pH—takes place within a short time even at room temperature and after the formation of about 25 to 27% isovincanol a state of equilibrium sets in.

The isovincanol amount of the injection prepared according to the invention does not exceed 4% related to the isovincanol content of the vincanol after 12 months which means an unexpected good stability.

The apovincaminic acid ethyl ester solution was tested on a Liquepump 312 equipment, detection wave length: 280 nm as an eluent a 70:30 mixture of acetonitrile and 0.01 molar aqueous ammonium carbonate solution is employed, flow rate: 1 ml./min.

TEST METHOD

Preparation of a Standard Solution 10 mg. of apovincamine and 10 mg. of vincaminic acid ethyl ester are measured to a 50 ml. measuring flask with an accuracy of 0.1 mg. The mixture is dissolved in acetonitrile and the solution is filled to the mark with acetonitrile. 5ml. of the stock solution are pipetted to a 100 ml. measuring flask and it is filled to the mark with acetonitrile. 20 μl of the solution are chromatographed.

20 μl. of the injection to be tested are chromatographed without dilution.

| Heat-treatment | | Total contamination | | |
|---|---|---|---|---|
| | | pH = 2.15 | pH = 3.35 | pH = 3.98+ |
| 25° C. | | 0.51% | φ | φ |
| 40° C. | 1 month | 1.12% | 0.23% | 0.13% |
| 50° C. | | 2.29% | 0.59% | 1.19% |
| 60° C. | | 9.63% | 1.55% | 1.69% |
| 100° C. | 1 hour | 0.32% | φ | 0.12% |
| 100° C. | 3 hours | 1.10% | 0.26% | 0.24% |
| 100° C. | 5 hours | 2.62% | 0.42% | 0.44% |

We claim:

1. A parenteral pharmaceutical composition which comprises as active ingredient a pharmaceutically effective amount of a compound of the formula (I)

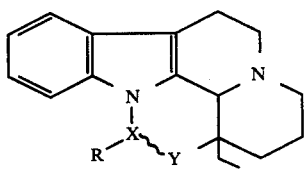

wherein
X⌢Y is

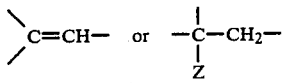

and

Z is hydroxy or cyano, and

R is hydrogen, an alkoxycarbonyl group having 2 to 6 carbon atoms which can be substituted by one or more halogen atoms or hydroxy groups or an aralkoxycarbonyl group, provided that if Z is hydroxy, then R is not simultaneously hdyrogen, along with a parenteral solvent which comprises (a) a pharmaceutically acceptable buffer or an organic acid having a $pK_a$ equalling 3 to 5 capable of adjusting the pH value of the parenteral composition to 2.5 to 5.0;

(b) at least one stabilizing agent selected from the group which consists of parenterally acceptable aliphatic alcohols containing one or more hydroxy groups and water-miscible ethers thereof;

(c) 30–70% by weight water; and (d) optional preservatives, anaesthetics or antioxidants.

2. The parenteral pharmaceutical composition defined in claim 1 wherein the aliphatic alcohols containing one or more hydroxy groups are selected from the group consisting of a $C_2$ to $C_6$ alkanol, a glycol, and a sugar alcohol.

3. The parenteral pharmaceutical composition defined in claim 1 wherein the water-miscible ether of the parenterally acceptable aliphatic alcohol containing one or more hydroxy groups is ethylene glycol monoethyl ether.

4. A method of treating a vascular flow disorder in an animal subject which comprises the step of administering to said animal subject a pharmaceutically effective amount of the parenteral composition defined in claim 1.

5. A parenteral pharmaceutical composition which comprises as active ingredient a pharmaceutically effective amount of vincanol along with a parenteral solvent which comprises (a) a pharmaceutically acceptable buffer mixture capable of buffering the pH of the parenteral composition to 7.5 to 9.5;

(b) at least one stabilizing agent selected from the group which consists of parenterally acceptable aliphatic alohols containing one or more hydroxy groups and water-miscible ethers thereof;

(c) 30–70% by weight water; and (d) optional preservatives, anaesthetics, or antioxidants.

6. The parenteral pharmaceutical composition defined in claim 5 wherein the aliphatic alcohols containing one or more hydroxy groups are selected from the group which consists of a $C_2$ to $C_6$ alkanol, a glycol and a sugar alcohol.

7. The parenteral pharmaceutical composition defined in claim 5 wherein the water-miscible ether of the parenterally acceptable aliphatic alcohol containing one or more hydroxy groups is ethylene glycol monoethyl ether.

8. A method of treating a vascular flow disorder in an animal subject which comprises the step of administering to said animal subject a pharmaceutically effective amount of the parenteral composition defined in claim 5.

* * * * *

UNITED STATES PATENT AND TRADEMARK OFFICE
CERTIFICATE OF CORRECTION

PATENT NO. : 4,344,950
DATED : 17 August 1982
INVENTOR(S) : Géza Takácsi Nagy et al It is certified that error appears in the above-identified patent and that said Letters Patent is hereby corrected as shown below:

In the heading, item [75], rewrite the first inventor's name to read:

-- Géza Takácsi Nagy --;

item [30], rewrite the priority date to read: -- 2 November 1979 --.

Col. 1, line 68, col. 2, line 24, col. 7, line 11, rewrite these lines to read:

-- X∼Y is --.

Col. 2, line 33, before "is" insert -- R --;

line 37, change "than" to -- then --.

Signed and Sealed this

Twenty-sixth Day of April 1983

[SEAL]

Attest:

Attesting Officer

GERALD J. MOSSINGHOFF

Commissioner of Patents and Trademarks